United States Patent [19]

Cano

[11] 4,000,257
[45] Dec. 28, 1976

[54] PROCESS FOR THE PURIFICATION OF INFLUENZA VIRUS VACCINE

[75] Inventor: Francis Robert Cano, Spring Valley, N.Y.

[73] Assignee: American Cyanamid Company, Stamford, Conn.

[22] Filed: Dec. 22, 1975

[21] Appl. No.: 642,942

[52] U.S. Cl. .................................................. 424/89
[51] Int. Cl.$^2$ ........................................ A61K 39/18
[58] Field of Search ................... 424/89; 195/1.5

[56] References Cited

UNITED STATES PATENTS 3,655,871   4/1972   Werner et al. ................ 424/89

*Primary Examiner*—Sam Rosen
*Attorney, Agent, or Firm*—Neal O. Willmann

[57] ABSTRACT

A process for producing high potency influenza vaccines with low pyrogenicity and low endotoxicity involves treating concentrated allantoic fluid (CAF) containing an attenuated virus sequentially with butyl acetate and ethyl acetate followed by flash evaporation.

7 Claims, No Drawings

PROCESS FOR THE PURIFICATION OF INFLUENZA VIRUS VACCINE

DESCRIPTION OF THE PRIOR ART

U.S. Pat. No. 3,627,873 (1971) teaches a method of preparing influenza vaccines having low pyrogenicity and high potency by treating the virus with solvents consisting of dilower alkyl ethers and lower alkyl esters of lower fatty acids. However, the reference only exemplifies extraction with diethyl ether and methyl acetate. Applicant has found that by employing a plurality of extractions with both butyl and ethyl acetates, he can achieve a significant increase in viral titer over the methyl acetate extraction disclosed in the prior art.

BRIEF SUMMARY OF THE INVENTION

A process for extracting pyrogens from an influenza vaccine is performed by treating a concentrated allantoic fluid (CAF) containing attenuated virus with a volume of butyl acetate equivalent to about 20% of the CAF volume at a temperature of about 15° to 25° C. for about 0.5 to 3.0 hours followed by separation of the CAF from the butyl acetate; repeating the extraction with another 20% portion of the butyl acetate; and the once-extracted CAF; repeating a third time with a 20% volume of ethyl acetate and the twice extracted CAF; and separating the thrice extracted CAF from the ethyl acetate for processing to a final vaccine.

DETAILED DESCRIPTION OF THE INVENTION

This invention discloses an improved process for producing influenza vaccines having reduced pyrogenicity, low endotoxicity and high chick cell agglutination (CCA) titers.

In accordance with the present invention, concentrated allantoic fluid (CAF) containing an attenuated virus such as influenza Type A [MRC-11 (Port Chalmas Strain)], Type B (B/X-1), Type A/Scotland/840/74 or Type A/Victoria/3/75 is treated with butyl acetate in an amount equal to about 20% of the CAF volume. The mixture is stirred for about 0.5 to 3.0 hours at a temperature of about 15° to 25° C. After this and all succeeding extractions, the mixture is placed in a chilled room for a period of 1 to 24 hours to facilitate separation of the phases. The butyl acetate phase is removed and discarded. The extraction is repeated with a second 20% portion of butyl acetate. The mixture is cooled, and the organic phase removed and discarded. Next, the CAF is treated with a volume of ethyl acetate equal to 20% of the CAF volume at 15° to 25° C. for 0.5 to 3.0 hours. The organic phase is, again, removed and discarded and the CAF is subjected to flash evaporation and restored to its original volume with sterile, pyrogen-free distilled water.

It is desirable, but not essential, that a small amount of wetting agent such as, polyoxyethylene sorbitan monooleate (Tween 80) be added. The amount is not critical and other physiologically acceptable wetting agents may be used.

The particular strain of virus used is not critical. Any strain normally used in the production of vaccines for human use is acceptable. For example, influenza viruses like B/Massachusetts/3/66, X-37A, A/Eng./42/72 or X-38A may also be used.

Influenza virus vaccine produced by the improved process of the present invention has certain distinct advantages over vaccines produced by the prior art process. The CCA titer (a measure of potency) is increased 4 to 6 times over the starting material for Type B virus and 2 to 3 times for Type A virus. This high CCA titer permits a higher dilution to arrive at the desired potency for human administration and therefore a more pure product. The pyrogenicity and endotoxicity of the product is also reduced to well below acceptable levels by the multiple extractions of the claimed process. The endotoxin content of the final vaccine is one one hundred times lower than the highest level permitted by U.S. Government regulations which means little, if any, patient reaction after administration. Processing the final vaccine after extraction also offers an advantage over the prior art because the virus need not be inactivated independently. This is achieved by the multiple extractions alone.

The following extractions were performed to illustrate the superiority of the particular procedure claimed in the present invention.

Table I

| Treatment | Viral Titer HA | Viral Titer CCA | Fold Increase in CCA Titer |
|---|---|---|---|
| Control (no extraction) | 9,600 | 2,237 | — |
| 2 BuAc — 1 EtAc (0.2 vol.) | 19,200 | 12,698 | 5.7 |
| 1 EtAc (0.1 vol.) | 9,600 | 9,330 | 4.2 |
| 1 EtAc (0.2 vol.) | 12,800 | 9,008 | 4.0 |
| 1 BuAc (0.1 vol.) | 19,200 | 8,888 | 4.0 |
| 1 BuAc (0.2 vol.) | 9,600 | 7,943 | 3.6 |
| 2 BuAc (0.2 vol.) | 9,600 | 6,348 | 2.8 |
| 2 EtAc (0.2 vol.) | 12,800 | 10,235 | 4.6 |
| 1 BuAc — EtAc (0.2 vol.) | 12,800 | 9,684 | 4.3 |

The results indicate a 5.7 fold increase in CCA titer for the multiple butyl and ethyl acetate extractions which is a significant increase over the 1.6 fold increase shown by Moyer in Example II, U.S. Pat. No. 3,627,873 (supra).

Comparative experiments with methyl acetate showed it to be far inferior to ethyl and butyl acetates in increasing viral titer. Also, methyl acetate was found to be extremely concentration dependent. For example, a 0.3 vol. sample contained only about one-third the viral titer of the 0.125 vol. sample. Butyl acetate was not sensitive to fluctuations and was therefore chosen for the initial extractions. Ethyl acetate was chosen for the final extraction because it will remove residual butanol in addition to pyrogens and endotoxins, and any residuum will be non-toxic ethanol. Also, methyl acetate was more dangerous to work with than the other two solvents.

EXAMPLE 1

Eleven day embryonated eggs are drilled in the air sac end and through this opening is injected 0.2 ml. of a dilution of Type A [MRC-11 (Port Chalmas Strain)] influenza virus previously titrated and calculated to produce maximum virus growth in 48-72 hours. The injected eggs are held at 34° C. at a relative humidity of 60-75% for 48-72 hours. At the end of the incubation period, the eggs are candled. The living eggs are chilled at 4° C. for 15 to 20 hours. The extra embryonic fluids are recovered and made into monovalent pools of a size which can be easily processed. The pooled fluids are clarified by low speed centrifugation and, if desired, 0.1% polyoxyethylene sorbitan monooleate is added. The fluid is then filtered through a final 0.45u filter prior to pelleting the virus with high speed centrifugation. The virus is then reconstituted at 25-40 times the concentration of the extra embryonic fluid. A volume of butyl acetate equal to 20% of the volume of the concentrated allantoic fluid (CAF) is added to the CAF and the mixture is stirred at 20° C. for one hour. This is allowed to stand in a chilled room for 12 hours or until the layers separate. The organic phase is separated and discarded. The extraction is repeated with a second 20% portion of butyl acetate. The organic layer is separated and discarded and a 20% volume of ethyl acetate is added to the CAF which is stirred at 20° C. for 1 hour. The organic phase is removed and the CAF is subjected to flash evaporation and then restored to its original volume with sterile distilled pyrogen-free water. The CCA value of the original CAF is 5050. The CCA value of the processed vaccine is 11,529 representing a two fold potency increase. The final vaccine is non-pyrogenic and essentially devoid of endotoxin when compared to government influenza standards. Inactivation with formaldehyde is unnecessary.

EXAMPLE 2

The procedure of Example 1 is repeated with the exception that the embryonated eggs are infected with Type B (BX-1) influenza virus. The CCA of the original CAF is 2,237. The CCA value of the final vaccine is 12,698 representing a more than five fold increase in potency. The final vaccine is well below government standards in pyrogenicity and endotoxin levels. Formaldehyde inactivation is, again, unnecessary.

I claim:
1. A process for extracting pyrogens and endotoxins from an influenza virus vaccine comprising:
   a. treating a concentrated allantoic fluid (CAF) containing live, attenuated virus by stirring with a volume of butyl acetate equivalent to about 10-30% of the CAF volume, at a temperature of about 15° to 25° C. for about 0.5 to 3.0 hours, followed by separation of the CAF from the butyl acetate;
   b. repeating step (a) with another 10-30% portion of butyl acetate and the once-extracted CAF;
   c. repeating step (a) with about 10-30% volume of ethyl acetate and the twice extracted CAF; and
   d. separating the thrice extracted CAF from the ethyl acetate for processing to a final vaccine.
2. The procedure of claim 1 wherein the extractions are performed with about a 20% portion of butyl acetate.
3. The procedure of claim 1 wherein the extractions are performed with about a 20% portion of ethyl acetate.
4. The procedure of claim 1 wherein the vaccine is Type A [MRC-11 (Port Chalmas Strain)].
5. The procedure of claim 1 wherein the vaccine is Type B (B/X-1).
6. The procedure of claim 1 wherein the vaccine is Type A/Scotland/840/74.
7. The procedure of claim 1 wherein the vaccine is Type A/Victoria/3/75.